(12) United States Patent
Andersson

(10) Patent No.: US 6,802,827 B2
(45) Date of Patent: Oct. 12, 2004

(54) HYPODERMIC IMPLANT DEVICE

(76) Inventor: Stig O. Andersson, 16165 Joplin Ave., Lakeville, MN (US) 55044

(*) Notice: Subject to any disclaimer, the term of this patent is extended or adjusted under 35 U.S.C. 154(b) by 254 days.

(21) Appl. No.: 10/183,723

(22) Filed: Jun. 25, 2002

(65) Prior Publication Data

US 2003/0004457 A1 Jan. 2, 2003

Related U.S. Application Data

(60) Provisional application No. 60/301,271, filed on Jun. 26, 2001.

(51) Int. Cl.[7] .......................... A61M 5/32; A61M 31/00
(52) U.S. Cl. .......................... 604/195; 604/198; 604/60
(58) Field of Search .............................. 604/57, 59, 60, 604/164.01, 195, 196, 198

(56) References Cited

U.S. PATENT DOCUMENTS

| 5,147,303 A | 9/1992 | Martin |
|---|---|---|
| 5,190,526 A | 3/1993 | Murray et al. |
| 5,211,628 A | 5/1993 | Marshall |
| 5,324,265 A | 6/1994 | Murray et al. |
| 5,395,346 A | 3/1995 | Maggioni |
| 5,411,487 A | 5/1995 | Castagna |
| 5,569,203 A | 10/1996 | Chen |
| 2001/0021821 A1 | 9/2001 | Wang et al. |
| 2001/0031940 A1 | 10/2001 | Loos |
| 2001/0037088 A1 | 11/2001 | Domici, Jr. et al. |
| 2001/0044599 A1 | 11/2001 | Lo |
| 2002/0010422 A1 | 1/2002 | Du Plessis |

*Primary Examiner*—Michael J. Hayes
(74) *Attorney, Agent, or Firm*—Gray, Plant, Mooty, Mooty & Bennett, P.A.; Malcolm D. Reid

(57) ABSTRACT

A hypodermic implant device, comprising a barrel; an upper piston segment engaged with an inner wall of the barrel; an axially aligned needle extendably distally out of the barrel for insertion into an object when the upper piston segment is moved distally within the body; a lower piston segment push rod in alignment with the needle, so that upon distal movement of the lower piston segment, the push rod moves distally through the needle expelling a releasable implant housed in the needle; and a means for retraction of the needle into a needle receptacle in the barrel.

11 Claims, 9 Drawing Sheets

Fig. 8 A
Fig 8 B
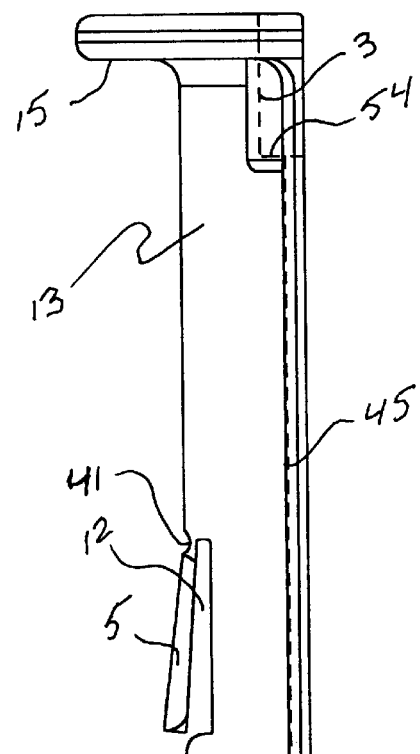
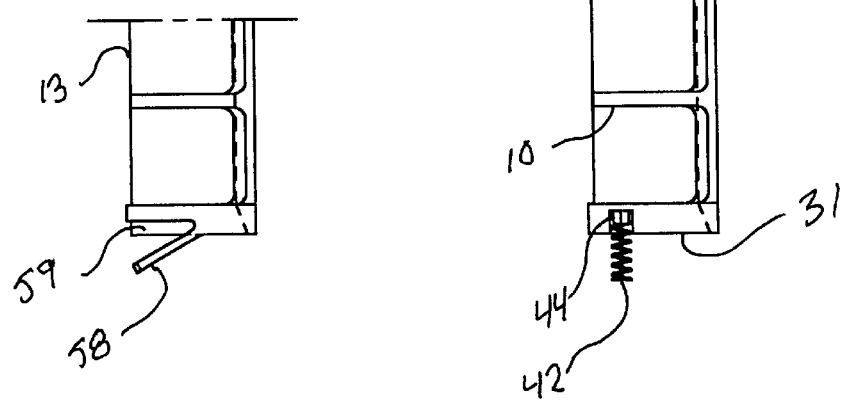

HYPODERMIC IMPLANT DEVICE

CROSS REFERENCE TO A RELATED APPLICATION

This application claims the benefit of U.S. Provisional Application No. 60/301,271, filed Jun. 26, 2001.

BACKGROUND OF THE INVENTION

1. Field of Use

The field of use for the hypodermic implant device described in this specification is for injecting implants into living or non-living organisms or things, such as inanimate articles and materials. Most often the implant device will be used for injecting an implant into subcutaneous tissues and blood vessels. The implant may be used for tracking and treatment of humans, animals, and plants. For purposes and illustration of an embodiment of the invention claimed in this specification, an application for the treatment of humans and animals will be described in the "Summary of an Embodiment of the Invention," the "Brief Description Of The Drawings", and the "Detailed Description And Operation Of The Invention" sections of this specification.

2. Description of the Related Art

Hypodermic implant devices are on the market today. They are used in clinical, surgical, and outdoor settings. However, the currently marketed hypodermic implant devices suffer from several shortcomings. Their extended needle poses a hazard of accidental needle sticks to the caregiver, the patient, and researchers. These devices do not have a nearly fail-safe method of self-destruction after use, thereby allowing possible reuse and the concomitant transmission of disease. Disposal of available implant device also poses risk of accidental needle sticks due to the extension of the islet or needle portion of the used implant device. The exposed islet also necessitates the use of special disposal containers for sharp contaminated articles. Furthermore, currently available hypodermic implant devices rarely feature a safety mechanism for locking the implant device to prevent accidentally expelling the implant. The invention described in this specification solves these needs.

SUMMARY OF AN EMBODIMENT OF THE INVENTION

With the proliferation of many blood borne contagious diseases, such as AIDS and Ebola, the frequent use of hypodermic implant devices poses a serious risk of infection. Many times, it is not possible to determine for an extended period of time whether a caregiver or researcher has been infected as a result of a needle sticks. The result can be actual infection with a sometimes-lethal blood borne pathogen or a prolonged period of anguish and worry only to discover that the user is not infected. Use of hypodermic implant devices pose significant risks in the everyday clinical practice of medicine, whether the patient be a human or some other specie of animal, and in the outdoor implantation of animals for research, tracking, or identification.

It has long been recognized that the needle stick risk factor needs to be controlled. Training and care while using hypodermic implant needles is emphasized. But, this, in of itself, is not enough, considering the high probability of a needle stick and the disastrous level of damage to health that it can inflict upon both the patient and caregiver. It is common practice in the health care or research industry to use a hypodermic implant device only once and then to dispose of it in a safe manner. However, currently marketed implant devices are not designed to self-destruct after a single use, thereby posing a risk of multiple uses. The hypodermic implant device of the present invention is designed so that it can be used once, only. Retraction of the piston of the device of the present invention results in retraction of the needle through and out of the luer fitting on the distal end of the barrel. The nozzle end of the needle then drops into a needle receptacle at the distal end of the barrel of the implant device making it virtually impossible to extend the needle outside the barrel. With the needle tilted into the distal end of the receptacle, the needle is simultaneously disabled from further use and safely disposed of; thereby avoiding transmission of infections by accidental needle sticks. Furthermore, in the clinic, hospital, veterinarian office, and farm or other field settings, the disposal of the implant device is much safer and may require a less costly disposal method than the currently used method of sharps disposal. The present invention features a normally retracted needle. This alone reduces risk of accidental needle sticks, since the needle is not exposed until it is actually ready to be injected into the target's tissue.

This invention also features a locking mechanism that prevents the needle from accidental extension beyond the barrel of the implant device. Extension of the needle requires the user to deliberately depress a tab-like lock, which is integrally molded into the piston. Depression of the lock into a lock space in the piston allows the lock to clear the inside diameter of the barrel, the piston to travel in axial alignment with and into the barrel, and extension of the needle beyond the distal end of the barrel.

This "Summary of an Embodiment Of The Invention" section describes the invention configured for implantation into humans and animals for purposes of illustration. It is to be understood that this invention may be used for myriad other applications.

BRIEF DESCRIPTION OF THE DRAWINGS OF AN EMBODIMENT OF THE INVENTION

FIG. 8A is a longitudinal view of the upper piston segment with a pre-load spring at its distal end of an embodiment of the hypodermic implant device of the present invention.

FIG. 8B is a partial longitudinal view of the upper piston segment illustrating the distal end of the segment with a pre-load device that is an alternative to the pre-load spring illustrated in FIG. 8A.

This "Brief Description of the Drawings of an Embodiment of the Invention" section describes an application for the treatment of humans and animals for illustration purposes only. It is to be understood that this invention may be used for myriad other applications.

DETAILED DESCRIPTION AND OPERATION OF AN EMBODIMENT OF THE INVENTION

Figure 1:
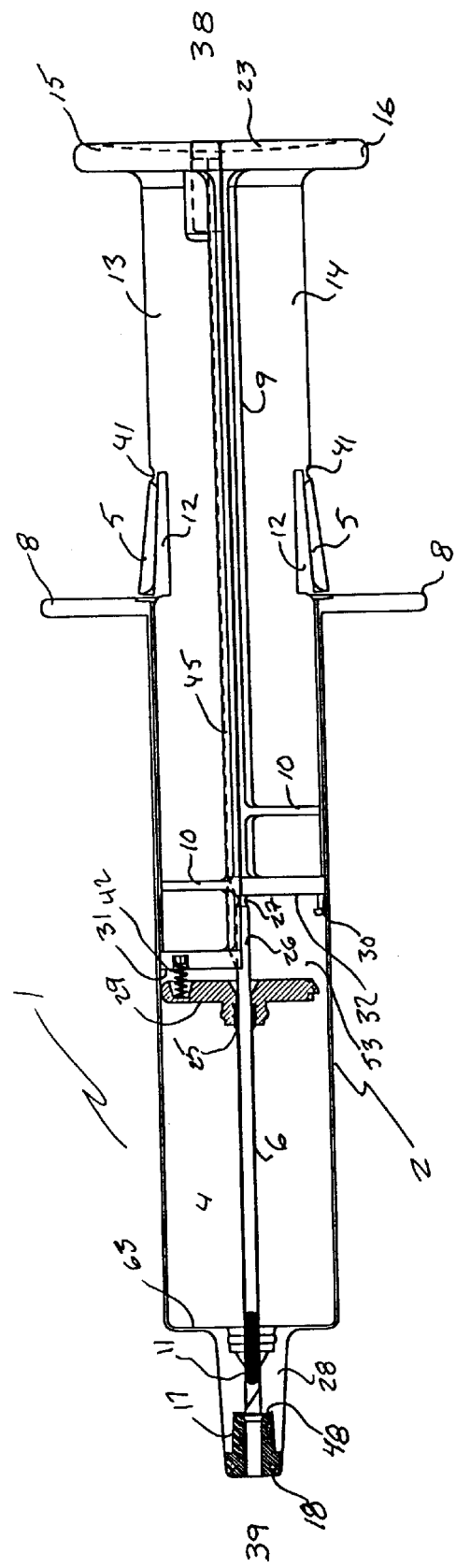
FIG. 1 is a partial sectional view along a plane parallel to the longitudinal axis of an embodiment of the hypodermic implant device with the piston in the rest position.

FIGS. 1 through 4 show the basic structure, assembly, and mode of operation of hypodermic implant device 1 of the present invention. FIG. 1 illustrates the initial state of device 1 when delivered, for example, in a sterile package to the user of implant device 1. Hypodermic device 1 as illustrated in FIG. 1 is comprised of barrel 2, piston 3, needle receptacle 4, lock 5, and needle 6. Barrel 2, piston 3, needle receptacle 4, and needle 6 are in axial alignment with one another along central axis 62. Piston 3 is split into two segments: upper piston segment 13 and lower piston segment 14. Needle 6 may be a stainless steel 300 Series, but any needle having a nozzle 20, a bore 22, and an inlet 21 may be suitable, depending upon the application. Piston 3 is locked in the position shown in FIG. 1 by locks 5. Locks 5, as shown in FIG. 1, are integrally molded into and is a part of piston 3. Locks 5 are connected to upper and lower piston segments 13 and 14 by tabs 41. Piston 3 and barrel 2 are plastic molded elements, using conventional plastic molding techniques. The types of plastics suitable for the implant device 1 are, for example, polycarbonate and polypropylene. These plastics are commercially available and currently used in the manufacture of hypodermic implant devices. These types of materials are sufficiently impact resistance to withstand the normally encountered forces and usage without sustaining damage. Substitute materials are also readily available for manufacture of device 1 for use in especially demanding environments, such as the research laboratory, outdoors, or in conjunction with injecting lubricants, adhesives, and other solids. When lock 5 is in its normal molded position, it is raised above the outside diameter of piston 3 and the inside diameter of barrel 2. In this position, the distal end of lock 5 engages with the proximal end of barrel 2, at the junction with barrel grip 8, to prevent piston 3 from sliding into barrel 2 by an axial force on piston 3 in the direction of the distal end of barrel 2. The term distal is used to refer to needle 6 end of hypodermic device 1 of the present invention. The term proximal is used to refer to the other end of device 1. Tab 51 is of a thickness that allows lock 5 to be relatively easily depressed by the user's finger when using implant device 1, yet thick enough that it will not be accidentally depressed during normal shipping, handling, and manipulation of device 1. In other words, it is of a thickness that requires a conscious effort to depress. Upon depression, lock 5 moves into lock depression space 12. Space 12 is of sufficient depth that when lock 5 is fully depressed it seats in space 12 with the upper surface of lock 5 at or below the outside diameter of piston 3, thereby allowing piston 3 to slide into barrel 2 upon application of a distally directed force on the piston. Since lock 5 is molded in the normally up position, i. e., at least the distal end of lock 5 is extended beyond the outside diameter of piston 3, it has memory that returns it to the normally up position when any downward force on lock 5 is relieved. The downward force is relieved when the user's finger pressure ceases or when piston 3 is pulled in a proximal direction relative to barrel 2 to the point where the distal end of lock 5 extends beyond the inner wall of barrel 2, thereby once again locking piston 3 so it cannot be extended into barrel 2 without further downward pressure on lock 5. The surface of lock 5 adjacent the outer wall of piston 3 is curved on the same radius as the outer wall of piston 3, which is the same radius as the inner wall of barrel 2. This allows for smooth travel of piston 3 into barrel 2.

Piston 3 locking feature prevents accidental extension of needle 6. If needle 6 is accidentally extended, it may be exposed to harmful pathogens or other substances and be damaged by blunting, bending, or scraping forces occurring in the working environment. More importantly, the exposure of needle 6, except when it must be extended for injection of an implant, increases the possibility of an accidental needle stick. Upon the occurrence of a needle stick, it is often not possible to determine whether an infectious substance was on needle 6. The resulting uncertainty, and in the case of AIDS months or years of waiting, whether the person experiencing the needle stick has become infected, is often the cause of untold anguish and disruption of the care giver's career. And, of course, the consequences of actual infection are often fatal and seriously life compromising during the period of sickness.

Upper and lower piston grip segments 15 and 16 provide an ergonomic thumb seat 23 for the user's thumb to rest during movement of piston 3 into barrel 2. The dotted line drawn on piston grip 7 in FIG. 1 is the depression, which forms the thumb seat 23.

Circumferentially placed around the outside periphery of piston 3 are four longitudinal ribs 9. Ribs 9 provide structural strength to piston 3. Ribs 9 allow piston 3 to be molded using less material than would be used if piston 3 diameter were substantially equal to the inside diameter of barrel 2 completely around the piston's entire circumference and along the piston's entire length. Additionally, the added friction between the surface of the outside diameter of piston 3 and the inside diameter of barrel 2, would require greater force to be applied to piston 3 to move piston 3 distally into barrel 2. With only ribs 9 providing contact with the inside surface of barrel 2, less force is required for movement of piston 3. Barrel grip 8 provides the user with a means to grip barrel 2 when depressing upper or lower piston segments 13 and 14 into barrel 2. The user's fingers grip the distal side of barrel grip 8 and the thumb depresses the respective upper or lower piston segment 13 or 14.

Piston rings 10 provide for circumferential support for piston 3 within barrel 2. The periphery of upper faceplate segment 31 and lower faceplate segment 32 also function to provide circumferential support. The additional support and the added friction assists with the smooth and tight fitting movement of piston 3 within barrel 2. Since each piston ring 10 is relatively narrow, the added friction is not great enough to require excessive force by the user to extend piston 3 into barrel 2. A gasket between needle receptacle 4 and the interface between piston 3 and barrel 2 is not needed for the hypodermic implant device 1, since there are no fluids in the device 1 as in a hypodermic injection device.

Support plate 29 supports the proximal end of needle 6 within barrel 2. Bonding material 25 bonds needle 6 into support plate 29. Support plate 29 is positioned relative to upper face plate segment 44 by pre-load spring 42, one end of which is seated in support plate spring seat 43 and the other end seated in upper face plate segment spring seat 44 as illustrated in FIGS. 1 through 4, 6, 8A, and 11. Needle receptacle 4 is formed in the distal interior end of barrel 2. The distal end of needle receptacle 4 terminates in luer sleeve 28 and the proximal end terminates in the combination of support plate 29 and upper and lower faceplate segments 31 and 32.

Figure 9:
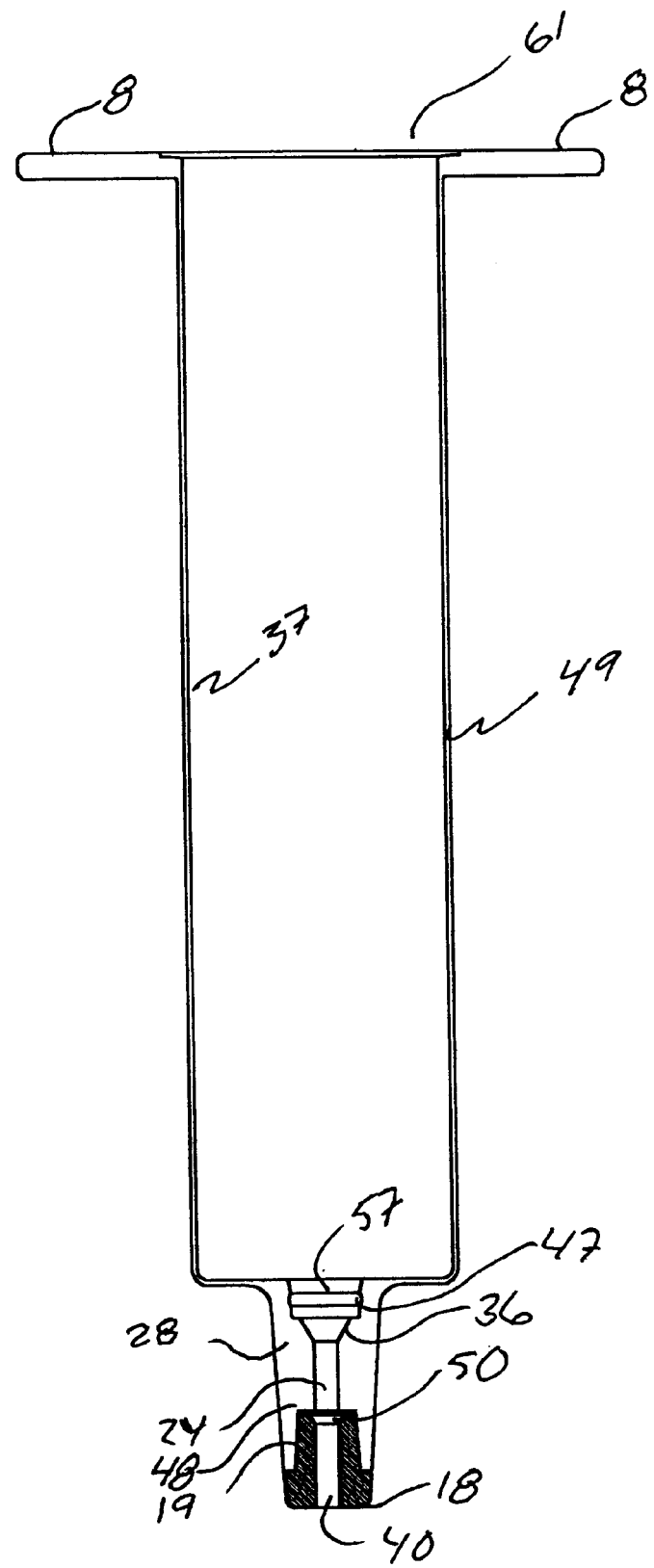
FIG. 9 is a longitudinal view along the axis of the barrel of an embodiment of the hypodermic injection device of the present invention.

Luer needle guide 24 supports the distal end of needle 6. Luer needle guide 24 extends through a portion of luer sleeve 28 as also shown in FIG. 9. Support plate plug 35 mates with support plate plug cavity 47 when upper piston segment 13 is in its most distal position. Support plate plug cavity 47 comprises support plate guide way 57 and support plate needle pilot 36 both of which axially connect to form support plate plug cavity 47, as illustrated in FIG. 9.

End cap 18 and seal 48 are inserted into end cap cavity 17. End cap 18 and seal 48 may either be friction fitted or bonded into end cap cavity 17. End cap 18 may be made of the same material as which the hypodermic implant device 1 barrel 2 and piston 3 are made or other suitable material that will allow end cap 18 to nonreleasably fit into end cap cavity 17. End cap 18 fixedly retains seal 48. Seal 48 can be made of the same or similar material as a septum used on a vial of an injectable drug. The septum of a drug vial allows the needle of a hypodermic injection device to be inserted through it for the purpose of withdrawing the medical fluid in the vial up into the injection device. Upon removal of all or a portion of the fluid from the vial, the septum seals itself, thereby maintaining the fluid safe from the environment and exposure to contamination. In implant injection device 1, seal 48 is a barrier that maintains needle 6 and implant 11 free from contaminants while they are in needle receptacle 4. But, it is a barrier that is easily penetrated by needle 6 when the user extends upper piston segment 13 in a distal direction to fully extend needle 6. Seal 48 is usually a silicone rubber material.

Needle guide 40 of end cap 18 and luer needle guide 24 are aligned with the central axis 62 of barrel 2. End cap 18 is provisioned with end cap needle pilot 50 for guiding needle 6 into end cap needle guide 40, as illustrated in FIG. 9. The combination of support plate plug cavity 57, support plate plug cavity 47, needle pilot 36, leur needle guide 24, seal 48 after perforation by extension of needle 6, end cap needle pilot 50, and needle guide-way 40 is referred to in this specification as needle guide-way 60.

Figure 2:
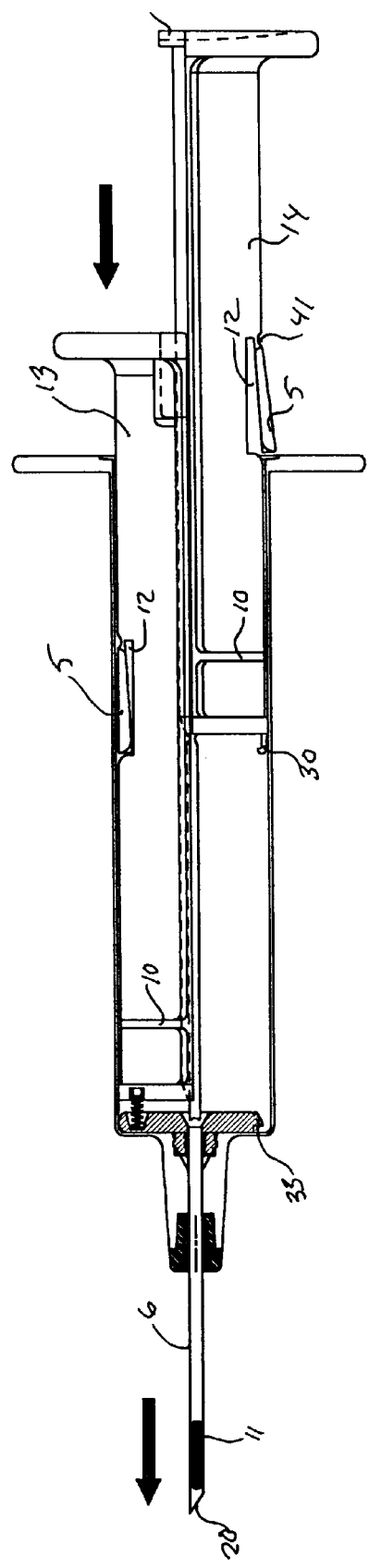
FIG. 2 is a partial sectional view along a plane parallel to the longitudinal axis of an embodiment of the hypodermic implant device with the upper piston segment of the split piston in the full needle extension position.
Figure 10:
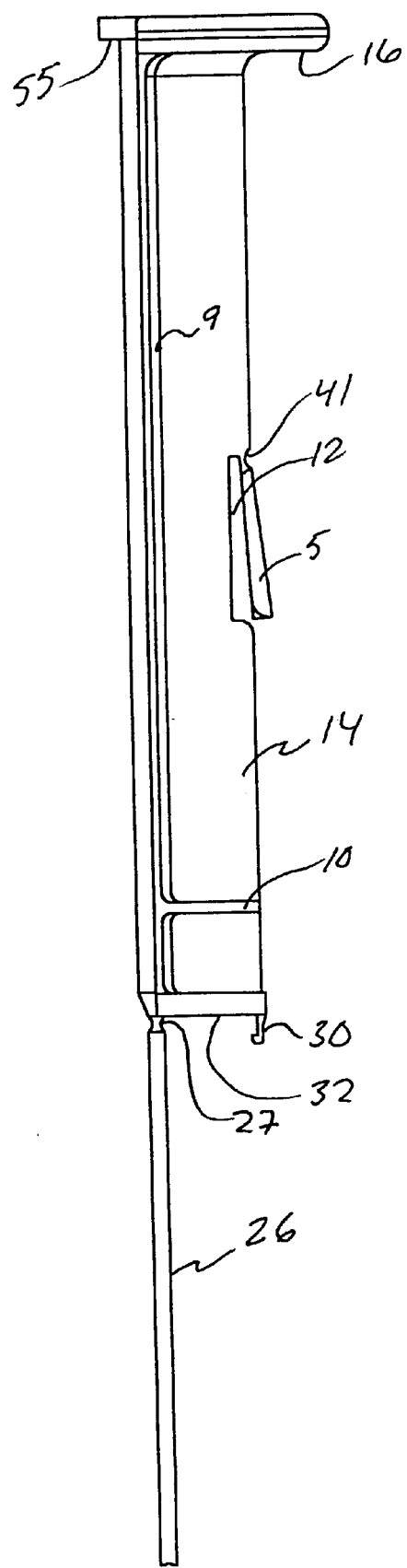
FIG. 10 is a longitudinal view of the lower piston segment of an embodiment of the hypodermic implant device of the present invention.

FIG. 2 illustrates hypodermic device 1 with needle 6 in the fully extended position. Needle 6 is positioned in the fully extended position by pushing upper piston segment 13 in the distal direction by using thumb pressure on upper piston grip segment 15 while grasping one or both barrel grips 8. Upper piston segment 13 and lower piston segment 14 are matingly and slidably engaged along their longitudinal interface by channel slide 45 and channel key 46, respectively. Channel slide 45, shown in FIG. 8A, may have a hemispherical cross-section or some other suitable shape that is capable of minimal binding with mating channel key 46. Channel key 46, as shown in FIG. 10, must have substantially the same shape as channel slide 45, but in reverse so that it matingly engages with channel slide 45. The fit between channel slide 45 and channel key 46 may vary from relatively loose to tight, depending upon the material from which each is fabricated. Generally, channel slide 45 and channel key 46 clearance may close if the material for both channel slide 45 and channel key 46 are fabricated of a plastic such as polycarbonate and polypropylene, as previously disclosed in this written description. Lock 5 of upper piston segment 13 is shown inside barrel 2 in a fully depressed position seated in lock depression space 12, thereby allowing upper piston segment 13 to slide within barrel 2. Nozzle 20 or distal end of needle 6 is out of its protective needle receptacle 4 portion of barrel 2 and piston 3 combination. Needle 6 penetrated seal 48 on its excursion through luer needle guide 24 and then continued on through end cap needle guide 40. Support plate plug 35 is extended into and mated with support plate plug cavity 47, thereby assisting the centering of needle 6 in luer needle guide 24 and end cap needle guide 40. Support plate 29 freely rides in barrel 2 since it has a diameter substantially equal to the inside diameter of barrel 6, providing a slidable but tight fit between support plate 29 and barrel 2. Support plate 29 is forced distally by upper faceplate segment 31 when piston 3 is moved distally. FIGS. 1 and 2 show the relationship of push rod 26 and needle bore 22. In FIG. 1, push rod 26 extends into bore 22 up to the proximal end of implant 11. Push rod 26 need not extend to implant 11, but by doing so it provides an efficient method of loading implant 11 into needle bore 22 during manufacture of hypodermic device 1. During manufacture, implant 11 can be inserted into needle bore 22 at the proximal end and then support plate 29, needle 6, and implant 11 combination inserted into barrel 2 from the proximal end. Next, upper and lower piston segments 13 and 14 are inserted into barrel 2 and pressed towards the distal end of hypodermic device 1 until they are stopped from further movement by their respective locks 5. Since push rod 26 is in axial alignment with needle bore 22, push rod 26 is automatically inserted into needle bore 22 as support plate 29, needle 6, and implant 11 combination is moved in a direction from the proximal end of device 1 to the distal end by movement of upper and lower piston segments 13 and 14 in that direction. In FIG. 1, push rod 26 is shown inserted into needle 6 and adjacent implant 11. FIG. 1 also illustrates that push rod 26 partially resides in channel slide 45 along a portion of its longitudinal length extending from lower face plate segment 32 to upper face plate segment 31. This is necessary because, as shown, both upper and lower piston segments 13 and 14 are cross-sectionally equal; yet push rod 26 (which is mounted on lower piston segment 14) must be axially aligned with needle bore 22 and barrel 2. Push rod 26 is affixed to lower face plate segment 32 by push rod taper 27, which allows for easy break-away or bending as will be described in connection with FIG. 4. The length of lower piston segment 14 is shorter than that of upper piston segment 13. And, as illustrated in FIG. 1, the resulting offset 53 between lower and upper piston segments 14 and 13 is positioned at the distal end of the two piston segments and not at their proximal end, so that lower face plate segment 32 is more proximal than that of upper face plate segment 31. The offset 53 is maintained at the distal end of the piston segments 14 and 13 by interlocking stop 54 and stop tab 55 in pistol grip 7, which is most easily observed in FIG. 3. Stop 54 and stop tab 55 in effect preset the location of offset 53 at the distal end of piston 3 by halting the travel of lower piston segment 14 relative to upper piston segment 13 since the distance that stop tab 55 can travel before its movement is halted by stop 54 is equal to the length of travel channel 56 (see FIG. 8A), which in turn is equal to the distance that lower and upper piston segments 14 and 13 are offset 53.

FIG. 2 illustrates implant device 1 in the first of three sequences of operation. In FIG. 2, needle 6 has been extended outside of needle receptacle 4, its protective sheaf. Pushing upper piston segment 13 in the distal direction as far as it will move extends needle 6. Prior to injection of implant 11, lock 5 on upper piston segment 13 had to be depressed as described in connection with FIG. 1. Movement of upper piston segment 13 is stopped when support plate 29 is adjacent the distal end of needle receptacle 4. In that position, push rod 26 has been extracted from needle bore 22. However, push rod 26 remains in support plate guide way 57 (See FIG. 6) for easy re-entry into needle 6 through needle inlet 21 due to the angled walls of guide way 57 towards needle inlet 21. Implant 11 remains in needle bore 22 at this stage of operation. Prior to pushing upper piston segment 13 distally, lock 5 must be depressed to allow segment 13 to travel into barrel 2. During distal movement of upper piston segment 13, its channel slide 45 traveled along channel key 46 allowing for smooth, low friction movement.

Figure 3:
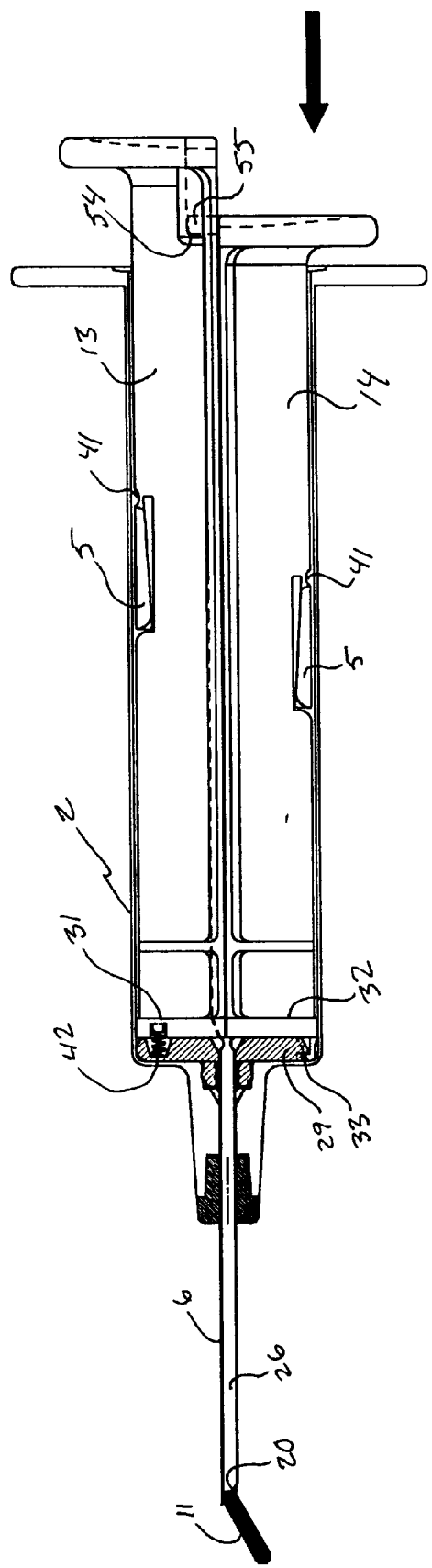
FIG. 3 is a partial sectional view along a plane parallel to the longitudinal axis of an embodiment of the hypodermic implant device with both the upper and lower segments of the split piston in the implant injection position.

FIG. 3 illustrates hypodermic device 1 after injection of implant 11. Lower piston segment 14 has been moved distally so that stop tab 55 is up against stop 54 retarding further movement. Further movement is also retarded by movement of lower faceplate segment 32 against the distal end of barrel 2. In this position, offset 53 between upper and lower faceplate segments 31 and 32 no longer exists as the offset now exists at the proximal end of piston 3. Distal movement of lower piston segment 14 caused movement of push rod 26 into needle bore 22. Since offset 53 is now absent at the distal end of piston 3, push rod 26 is able to travel further into needle 6 than it could in the position shown in FIG. 1 by the length of offset 53. The added length of penetration of push rod 26 causes implant 11 to be ejected out of needle nozzle 20 and into the patient, other subject, or object. FIG. 3 also illustrates that upper and lower face plate segments 31 and 32 and support plate 29 are now in an abutting relationship, whereas in FIGS. 1 and 2 there was space between them. That space was maintained by the force of preload spring 42. In the position shown in FIG. 3, pre-load spring 42 will cause upper faceplate segment 31 to separate from support plate 29 once the user of device 1 releases force on piston 3. Release of the force, however, will not cause uniform separation between support plate 29 and the combination of upper face plate segment 31 and lower face plate segment 32 because hook 30 on lower face plate segment 32 has engaged undercut 33 on the distal face of support plate 29. As will most often be the case, the user will inject implant 11 and then immediately proceed to retract piston 3.

Figure 4:
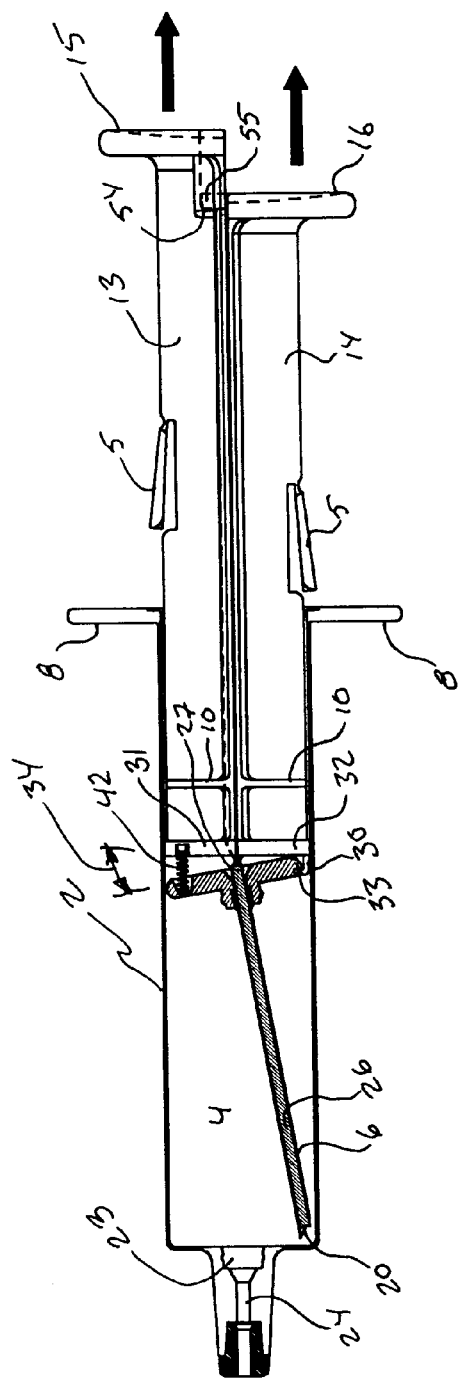
FIG. 4 is partial sectional view along a plane parallel to the longitudinal axis of an embodiment of the hypodermic implant device with the upper and lower piston segments fully retracted with the needle tilted into the needle receptacle for safe disposal and for self destruction of the implant injection device, thereby limiting the device to a single use.

FIG. 4 illustrates implant device 1 in its final state of use and ready for disposal. In this position, needle 6 is fully retracted from support plate plug cavity 47 into the safety of needle receptacle 4 by the user's retraction of upper piston segment 13, which causes lower piston segment 14 to also retract due to the interaction of stop 54 and stop tab 55. As mentioned in the previous paragraph, when the distally driven force on piston 3 is relieved, pre-load spring 42 will cause the upper portion of support plate 29 to tilt within needle receptacle 4 due to engagement, during the injection phase illustrated in FIG. 3, of undercut 33 by hook 40. Since there is nothing supporting the distal end of needle 6 at this point, it falls down into needle receptacle 4 where it can no longer be extended outside barrel 2. Implant device 1 is no longer usable and is ready for disposal with needle 6 already in a sharps container-needle receptacle 4—protecting living beings or property from damage caused by sharp needle 6.

During the injection phase, resilient hook 30 is forced to ride up on ramp 52 (shown in FIG. 6) of support plate 29 to the point where it reaches undercut 33, at which point resilient hook 30 snaps into undercut 33 and engages the lower portion of support plate 29. Upon full retraction of needle 6 into needle receptacle 4, the force of pre-load spring 42 forces supports plate 29 to tilt at tilt angle 34. Tilt angle 34 in one embodiment approximates 10 degrees. Tilting of support plate 29 is also assisted by the differential friction between the upper portion of circumferential rim 60 of support plate 39 and barrel wall 37. There is no friction between the lower portion of circumferential rim 60 of support plate 39 and barrel wall 37 in the region of undercut 42 because undercut 42 is located on a chord 58 of support plate 39 and chord 58 does not contact barrel wall 37. Chord 58 is best illustrated in FIGS. 8A, 8B, 9C, and 10C. The location of chord 58 in barrel 2, shown in FIGS. 1 through 5, is located towards the bottom of each of the figures. Therefore, that area exerts the least frictional force and tipping occurs elsewhere with hook 40 and undercut 42 acting as the fulcrum.

Little resistance to this tilting force is encountered from push rod 26, which remains in needle bore 22, since it is connected to lower face plate segment 32 by relatively thin push rod taper 27. The result of the tilting action is that nozzle 20 end of needle 6 tilts against a wall of barrel 2 and is restrained by distal end of barrel 2 from entering support plate plug cavity 23 and being further extended outside of needle receptacle 4 for further use. Even an active attempt to shake needle 6 into alignment with support plate plug cavity 23 will not be met with success due to force of pre-load spring 42 maintaining needle 6 in the position shown in FIG. 4. Retraction of piston 3 is accomplished by exerting a force directed in the proximal direction on either upper and lower piston segments 13 and 14 or only upper piston segment 13. In either case as the piston segments are pulled proximally, stop 54 will engage stop tab 55 and cause lower piston segment 14 to ride along. Upon retraction of piston 3, support plate 39 is pulled along with piston 3 in the proximal direction by hook 40 on faceplate 41.

Figure 5:
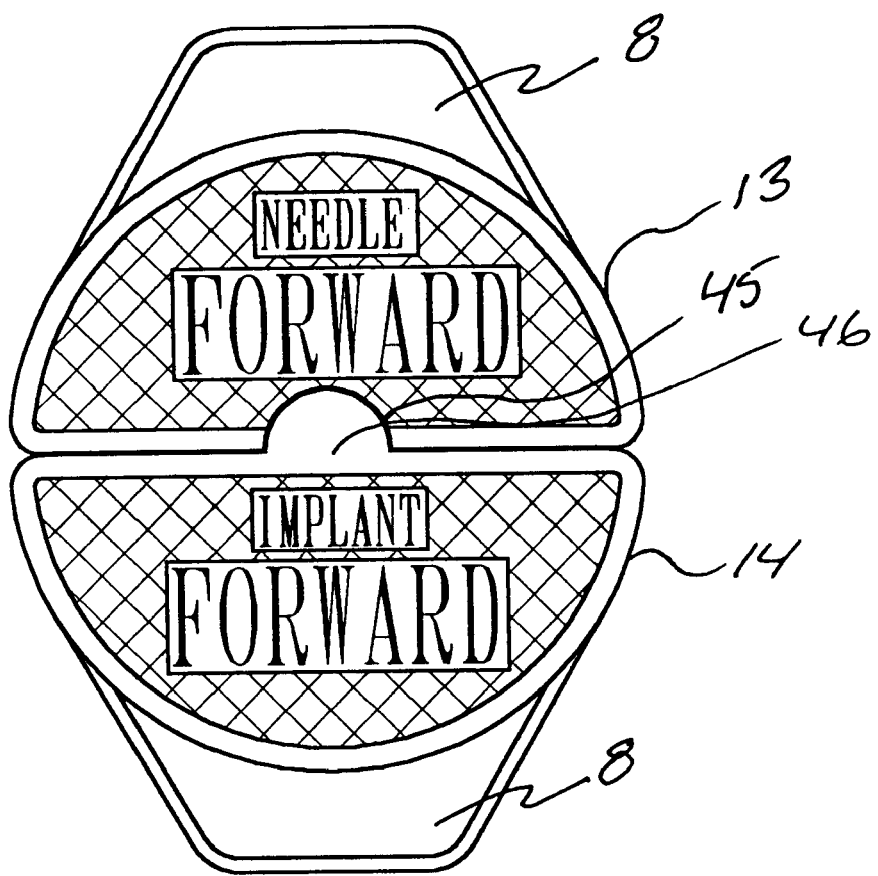
FIG. 5 is a plan view of the proximal end of the barrel and the split piston of an embodiment of the hypodermic implant device of the present invention with an exemplar of user directions for extension of the needle and then for insertion of the implant.

FIG. 5 illustrates an example of simple instructions marked on the proximal end of piston grip 7.

Figure 6:
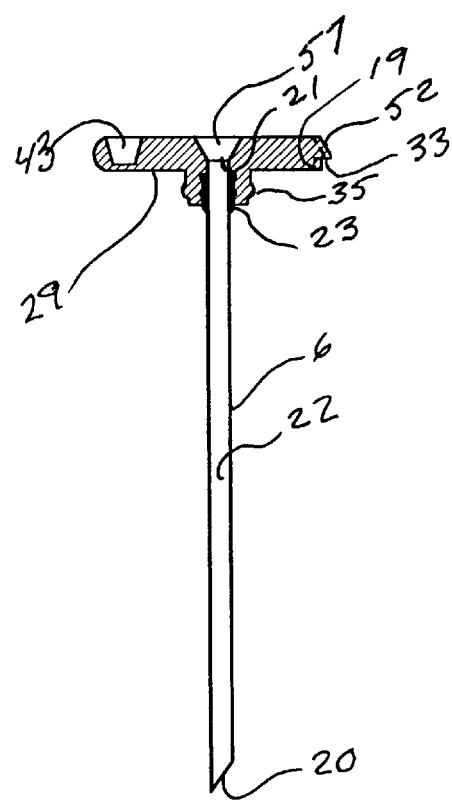
FIG. 6 is an axial cross section view of the needle and its support plate of an embodiment of the hypodermic implant device of the present invention.
Figure 7:
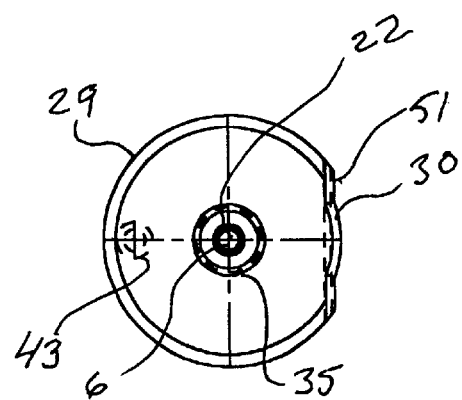
FIG. 7 is a plan view of the distal end of the needle support plate of an embodiment of the hypodermic implant device of the present invention.

FIGS. 6 and 7 illustrate more clearly the details of support plate 29 and needle 6 combination. Undercut 33 is along chord 51 of support plate 35 as is ramp 52. Hook 30 is clearly seen in FIG. 7 as engaged with undercut 33 and as having an arcuate wall to conform to the diameter of barrel wall 37 with which it matingly engages and travels against during movement of lower piston segment 14.

FIGS. 8A, 8C, and 8D illustrate the particular details of upper piston segment 13 more clearly than possible in FIGS. 1 through 4. FIG. 8B illustrates an alternative embodiment to pre-load spring 42. Pre-load lever 58 is made of the same resilient plastic material, as previously described, as are the other elements of hypodermic implant device 1. Pre-load lever 58 is integrally molded into upper faceplate segment 31 and is seated into pre-load lever seat 59 when compressed as shown in FIG. 3. Pre-load spring 42 and pre-load lever and 58 represent two illustrated embodiments of a biasing means for tilting support plate 29, but any means that accomplishes the function of tilting support plate 29 is contemplated by this invention. Such a means could include no biasing method other than the frictional force between the upper portion of support plate 29 and barrel wall 37 coupled with engagement of hook 30. FIGS. 9, 10A, 10B, and 10C illustrate the particular details of the barrel 2 and lower piston segment 14 more clearly than possible in FIGS. 1 through 4. FIG. 11 illustrates the general assembly of implant device 1.

This "Detailed Description And Operation Of The Invention" section describes the invention configured for implantation into humans and animals for purposes of illustration. It is to be understood that this invention may be used for myriad other applications. One skilled in the art can make changes in structure, material, and arrangement of structures without departing from the invention.

What I claim is:

1. A hypodermic implant device, comprising: (a) a barrel comprising an open end and a guide-way end, the centers of the open end and the guide-way end in alignment with a central axis of the barrel; (b) a piston, comprising an upper piston segment and a lower piston segment, matingly engaged with an inner wall of the barrel for sliding movement in alignment with the central axis; (c) a central axis aligned needle with its inlet end facing the distal end of the piston and its nozzel end supported in the guide-way; (d) a needle receptacle comprised of a space formed by the barrel inner wall, the distal inner end of the barrel, and the distal face of the piston, so that when the upper piston segment is moved distally within the barrel, the nozzel extends distally through the guide-way out of the needle guide-way in position for insertion of the needle into an object; (e) a central axis aligned lower piston segment push rod in alignment with the needle bore, so that when the lower piston segment is moved distally within the barrel, the push rod moves distally through the needle bore expelling a releasable implant housed in the needle bore; and (f) a means for engagement of the needle inlet end to the distal face of at least one of the piston segments, so that the nozzel is fully retracted into the needle receptacle upon retraction of at least one of the piston segments.

2. A hypodermic implant device, comprising: (A) a barrel comprising an open end, a closed end, an outer wall, an inner wall, an annular barrel grip extending in a radial direction from the barrel outer wall at the open end, a luer sleeve at the closed end, an end cap in the leur sleeve, a seal in abutting engagement with the end cap and the luer sleeve, and a guide-way extending through the luer sleeve and the end cap, all of which are in axial alignment with a central axis, the guide-way comprising (i) a support plate plug guide-way, (ii) a support plate plug cavity, (iii) a needle pilot, (iv) a luer needle guide, (v) a seal after perforation by the needle, (vi) an end-cap needle pilot; and (vii) a needle guide-way; (B) a piston in alignment with the central axis engaged with the inner wall for axial sliding movement with the inner wall, the piston comprising (a) an upper piston segment comprising (i) a stem portion with at least one rib extending longitudinally along the stem portion, (ii) a split piston grip extending in a radial direction from the upper piston segment stem and rib combination with a diameter exceeding that of the outer wall of the barrel, (iii) a lock attached to the upper piston segment by a tab for depression into a depression space of a depth sufficient to allow the lock to clear the diameter of the inner wall allowing the upper piston segment to be extended into the barrel and upon retraction of the upper piston segment allowing the lock to return to a normal raised position beyond the diameter of the inner wall, thereby releasably locking the upper piston segment from axial extension into the barrel, (iv) at least one piston ring, the diameter of which is substantially equivalent to the diameter of the inner wall, engaged for axial sliding movement with the inner wall, (v) a distally located upper face plate segment with a seat for seating a preload spring, the diameter of the upper face plate segment substantially equivalent to the diameter of the inner wall for axial sliding movement of the upper face plate segment with the inner wall, (vi) a channel slide extending longitudinally along a diameter of the upper piston segment, (vii) a travel channel recessed in the upper piston grip segment terminating at its distal end in a stop; (b) a lower piston segment comprising (i) a stem portion with at least one rib extending longitudinally along the stem portion, (ii) a split piston grip extending in a radial direction from the lower piston segment stem and rib combination with a diameter exceeding that of the outer wall of the barrel, (iii) a lock attached to the lower piston segment by a tab for depression into a depression space of a depth sufficient to allow the lock to clear the diameter of the inner wall allowing the lower piston segment to be extended into the barrel and upon retraction of the lower piston segment allowing the lock to return to a normal raised position beyond the diameter of the inner wall, thereby releasably locking the lower piston segment from axial extension into the barrel, (iv) at least one piston ring, the diameter of which is substantially equivalent to the diameter of the inner wall, engaged for axial sliding movement with the inner wall, (v) a distally located lower face plate segment comprising a diameter substantially equivalent to the diameter of the inner wall for axial sliding movement with the inner wall and the diameter chord of the upper piston segment and a push rod in alignment with the needle bore, so that when the lower piston segment is moved distally within the barrel, the push rod moves distally through the needle bore expelling a releasable implant housed in the needle bore, (vi) a channel key extending longitudinally along the lower piston segment diameter chord for mating engagement with the channel slide, (vii) a stop tab depending from the proximal end of the lower piston grip segment for mating engagement with the upper piston grip segment; and (viii) a lower face plate segment on the distal end, comprising a diameter, substantially equivalent to the diameter of the inner wall, engaged with the inner wall for axial sliding movement and a pheripherally depending hook; (C) a support plate for supporting the needle in a longitudinal direction on the central axis comprised of an inlet in line with the central axis and in communication with a bore of the needle, a support plate plug for mating engagement with the support plate plug cavity when the upper piston segment is fully extended into the barrel, the needle bonded into a bonding recess located in the distal face, an undercut on a chord for engagement with the hook when the lower piston segment is in abutting contact with the support plate and the support plate is positioned in abutting contact with the inner end of the barrel; (D) the needle, in alignment with the central axis with the proximal end of the needle facing the distal end of the piston and with the distal end of the needle supported in the luer needle guide, the needle having a length such that when at least the upper piston segment is retracted out of the barrel beyond a locked position with respect to the barrel, the needle retracts from the leur needle guide and from the support plate plug cavity and the nozzel is contained within a needle receptacle; and (E) the needle comprised of a length that is directly related to the longitudinal distance between the lock on the upper piston segment and the face plate when the upper piston segment is in the locked position in the barrel.

3. A method of implanting using the hypodermic implant device of claim 2, comprising the steps of: (a) with upper and lower piston segments locked into an initial position longitudinally with respect to the barrel, the distal end of the needle supported in the needle guide-way, an implant in the needle bore, and the upper face plate segment interconnected with the support plate by preload spring, depressing the upper piston segment lock and then sliding the upper piston segment with interconnected support plate in a distal direction to the inner end of the barrel to extend the needle beyond the distal end of the end cap; (b) extending the needle into an object to be implanted; (c) depressing the lower piston segment lock and then sliding the lower piston segment with interconnected push rod in a distal direction to the inner end of the barrel to engage the hook with the undercut on the support plate chord and extend the push rod into the needle bore to inject the object with the implant; and (d) retracting the piston from the barrel in a proximal direction to a point where the locks are beyond the barrel open end, so the distal end of the needle falls within the needle receptacle.

4. A hypodermic implant device comprising: (a) a barrel; (b) a piston slidable within the barrel comprised of an upper piston segment for moving a needle beyond the distal end of an end cap and a lower piston segment having a push rod in alignment with the central axis for moving an implant beyond a nozzel; (c) a needle receptacle; (d) a needle with an implant in a bore, the nozzel end of the needle supported in a needle guide-way, the proximal end of the needle facing the distal end of the piston for abutable contact therewith, and the needle of a length that will allow the needle to be contained in the needle receptacle when the distal end of the needle is retracted from a guide-way; and (e) a means of engagement of the proximal end of the needle with the distal end of the lower piston segment for retraction of the nozzel end of the needle from the guide-way.

5. The hypodermic implant device of claim 4, in which the upper and lower piston segments further comprise locks attached to each piston segment for manual depression into a depression space, the depth of the depression space sufficient to allow the locks when depressed to clear the piston diameter thereby allowing the respective piston segments to extend into the barrel, and upon retraction of the respective piston segment, the lock automatically returns to its normally raised position so the respective piston segment is again locked from axial extension into the barrel.

6. The hypodermic implant device of claim 5, in which the upper and lower piston segments each further comprise (i) a stem, (ii) with at least one rib extending longitudinally along the stem, (iii) a piston grip extending in a radial direction from the piston stem and rib combination with a diameter exceeding that of the piston stem and rib combination, and (iv) at least one piston ring, the diameter of which is substantially equivalent to the diameter of the inner wall, engaged for axial sliding movement within the inner wall.

7. The hypodermic implant device of claim 5, in which the means of engagement of the proximal end of the needle with the distal end of the piston for retraction of the distal end of the needle from the guide-way further comprises: a lower face plate segment on the distal end, comprising a diameter, substantially equivalent to the diameter of the inner wall, engaged with the inner wall for axial sliding movement and a pheripherally depending hook; a support plate for supporting the needle in a longitudinal direction on the central axis comprised of an inlet in line with the central axis and in communication with a bore of the needle, a support plate plug for mating engagement with the support plate plug cavity when the upper piston segment is fully extended into the barrel, the needle bonded into a bonding recess located in the distal face, an undercut on a chord of the support plate for engagement with the hook when the lower piston segment is in abutting contact with the support plate and the support plate is moved distally within the barrel in abutting contact with the inner end of the barrel.

8. The hypodermic implant device of claim 5, wherein the needle receptacle comprises the space between the distal end of the barrel and the distal end of the upper and lower face plate segments when the upper and lower piston segments are retracted so that there is no offset space between the upper and lower face plate segments.

9. A method of implanting using the hypodermic implant device of claim 5, comprising the steps of: (a) with upper and lower piston segments locked into an initial position longitudinally with respect to the barrel, the distal end of the needle supported in the needle guide-way, an implant in the needle bore, and the upper face plate segment interconnected with the support plate by preload spring, depressing the upper piston segment lock and then sliding the upper piston segment with interconnected support plate in a distal direction to the inner end of the barrel to extend the needle beyond the distal end of the end cap; (b) extending the needle into an object to be implanted; (c) depressing the lower piston segment lock and then sliding the lower piston segment with interconnected push rod in a distal direction to the inner end of the barrel to engage the hook with the undercut on the support plate chord and extend the push rod into the needle bore to inject the object with the implant; and (d) retracting the piston from the barrel in a proximal direction to a point where the lock is beyond the barrel open end, so the distal end of the needle falls within the needle receptacle.

10. The hypodermic implant device of claim 4, in which the means of engagement of the proximal end of the needle with the distal end of the piston for retraction of the distal end of the needle from the guide-way further comprises: (a) a lower face plate segment on the distal end of the lower piston segment with a hook at the periphery of the lower face plate segment for hooking a support plate when the lower piston segment is fully extended into the barrel; and (b) a support plate, for supporting the needle in a longitudinal direction on the central axis, comprised of an inlet in line with the central axis and in communication with a bore of the needle and the proximal face of the support plate, a support plate plug for mating engagement with a support plate plug guide-way when at least the upper piston segment is fully extended into the barrel, the needle bonded into a bonding recess located in the distal face of the support plug, and an undercut on a chord for engagement with the hook when the lower piston segment is extended fully within the barrel.

11. The hypodermic implant device of claim 4, in which the barrel is comprised of an open end, an annular barrel grip extending in a radial direction from the barrel outer wall at the open end, a luer sleeve at the distal end of the barrel in alignment with the central axis of the barrel, an end cap in the distal end of the luer sleeve in alignment with the central axis, a seal in alignment with the central axis in abutting engagement with the luer sleeve and end cap, and a guide-way in alignment with the central axis extending through the luer sleeve and the end cap, the guide-way comprising (i) a support plate plug guide-way, (ii) a support plate plug cavity, (iii) a needle pilot, (iv) a luer needle guide, (v) the seal after perforation by the needle, (vi) an end-cap needle pilot; and (vii) a needle guide-way.

* * * * *